US009241645B2

(12) United States Patent
Miyazaki

(10) Patent No.: US 9,241,645 B2
(45) Date of Patent: Jan. 26, 2016

(54) MULTIPLE MR FLUID FLOW IMAGING AT PREDETERMINED TEMPORAL RESOLUTION WITHIN SELECTED PERIOD OF CARDIAC CYCLE DETERMINED BY MULTIPLE MR IMAGING AT DIFFERENT TEMPORAL RESOLUTION

(71) Applicant: Mitsue Miyazaki, Des Plaines, IL (US)

(72) Inventor: Mitsue Miyazaki, Des Plaines, IL (US)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 257 days.

(21) Appl. No.: 13/633,503

(22) Filed: Oct. 2, 2012

(65) Prior Publication Data

US 2013/0102881 A1   Apr. 25, 2013

Related U.S. Application Data

(63) Continuation-in-part of application No. 12/923,892, filed on Oct. 13, 2010, now Pat. No. 8,543,187.

(30) Foreign Application Priority Data

Oct. 13, 2011   (JP) ................. 2011-226171

(51) Int. Cl.
*A61B 5/05* (2006.01)
*A61B 5/026* (2006.01)
*A61B 5/055* (2006.01)
*A61B 5/00* (2006.01)
(Continued)

(52) U.S. Cl.
CPC ............. *A61B 5/0263* (2013.01); *A61B 5/0037* (2013.01); *A61B 5/0044* (2013.01); *A61B 5/055* (2013.01); *A61B 5/742* (2013.01); *G01R 33/4838* (2013.01); *G01R 33/5635* (2013.01); *G01R 33/56308* (2013.01); *A61B 5/7285* (2013.01); *A61B 2576/00* (2013.01)

(58) Field of Classification Search
None
See application file for complete search history.

(56) References Cited

U.S. PATENT DOCUMENTS

| 5,054,489 A | 10/1991 | Axel et al. |
| 6,192,264 B1 | 2/2001 | Foo et al. |
| 6,781,375 B2 | 8/2004 | Miyazaki et al. |

(Continued)

FOREIGN PATENT DOCUMENTS

| JP | 2005-305151 A | 11/2005 |
| JP | 2006-158512 | 6/2006 |

(Continued)

OTHER PUBLICATIONS

Miyazaki, et al., "Non-contrast-enhanced MR angiography using 3D ECG-synchronized half-Fourier fast spin echo," *JMRI*12:776-783 (2000).

(Continued)

*Primary Examiner* — James Kish
(74) *Attorney, Agent, or Firm* — Nixon & Vanderhye P.C.

(57) ABSTRACT

A magnetic resonance imaging apparatus according to an exemplary embodiment includes a determining unit and an imaging unit. When a fluid traveling through a subject is imaged for multiple times at different phases, the determining unit determines a period on the time axis within which imaging is performed at intervals satisfying a predetermined temporal resolution. The imaging unit performs imaging for multiple times by the temporal resolution within the period.

10 Claims, 11 Drawing Sheets

(51) Int. Cl.
*G01R 33/483* (2006.01)
*G01R 33/563* (2006.01)

(56) References Cited

U.S. PATENT DOCUMENTS

| | | | |
|---|---|---|---|
| 7,965,079 B2 | 6/2011 | Furudate | |
| 2002/0060566 A1 | 5/2002 | Debbins et al. | |
| 2004/0155653 A1 | 8/2004 | Larson et al. | |
| 2006/0183999 A1* | 8/2006 | Lorenz et al. | 600/410 |
| 2008/0009705 A1 | 1/2008 | Furudate | |
| 2008/0081987 A1* | 4/2008 | Miyazaki | 600/410 |
| 2008/0265884 A1 | 10/2008 | Miyazaki | |
| 2009/0005670 A1 | 1/2009 | Ichinose et al. | |
| 2009/0148020 A1 | 6/2009 | Sugiura | |
| 2009/0149734 A1 | 6/2009 | Sugiura | |
| 2010/0198046 A1* | 8/2010 | Takei | 600/410 |
| 2010/0249574 A1 | 9/2010 | Miyazaki | |

FOREIGN PATENT DOCUMENTS

| | | |
|---|---|---|
| JP | 2008-23317 A | 2/2008 |
| JP | 2008-086747 A | 4/2008 |
| JP | 2009-28525 | 2/2009 |
| JP | 2009-153965 | 7/2009 |
| JP | 2010-022813 A | 2/2010 |
| WO | WO 88/07349 | 10/1988 |

OTHER PUBLICATIONS

Furudate, et al., "FBI-Navi for Easy Determination of Diastolic and Systolic Triggering Phases in Non-Contrast Fresh Blood Imaging (FBI)," ISMRM 16*th* Annual Meeting, Toronto, p. 2902 (2008).

Miyazaki, et al., "Peripheral MR angiography: Separation of Arteries from Veins with Flow-spoiled Gradient Pulses in Electrocardiography-triggered Three-dimensional Half-Fourier Fast Spin-Echo Imaging," *Radiology* 227:890-896 (2003).

Nakamura, et al., "Flow-Motion FBI, a novel non-contrast-enhanced 3D-MRDSA technique using ECG-Triggered Three-Dimensional Half-Fourier FSE—the feasibility to evaluate hemodynamics of peripheral vascular diseases," Proc. Intl. Soc. *Mag. Reson. Med.* 13, p. 1713 (2005).

Nakamura, et al., "Feasibility of quantitative analysis of non-contrast-enhanced MRDSA using ECG-gated two-dimensional half-Fourier FSE for the assessment of peripheral vascular diseases," Proc. Intl. Soc. *Mag. Reson. Med. 14*, presented at the ISMRM 14th Annual Meeting, Seattle, Washington, p. 1933 (2006).

Gharib et al., "Coronary MR Angiography 3T During Diastole and Systole", *Proc. Intl. Soc. Mag. Reson.Med. 14*, p. 2164 (2006).

P. Lai et al., "Respiratory Self-gated 4D Coronary MRA", *Proc. Intl. Soc. Mag. Reson. Med.*, 14, p. 364 (2006).

Bi et al., "A fully automated selection of the optimal data acquisition window in coronary MRA eliminating the need for user-interaction", *Proc. Intl. Soc. Mag. Reson. Med. 15*, p. 2488 (2007).

Fung et al., "Multi-phase Fat Suppressed 3D SSFP for Robust Coronary Artery Imaging: Improvements over the single phase technique", *Proc. Intl. Soc. Mag. Reson. Med. 16*, p. 313 (2008).

Miyazaki et al., "Nonenhanced MR Angiography", *Radiology*, vol. 248, No. 1, pp. 20-43 (2008).

Office Action dated Dec. 19, 2012 in U.S. Appl. No. 12/923,892.

Kanazawa et al., "Time-Spatial Labeling Inversion Tag (t-SLIT) using a Selective IR-Tag On/Off Pulse in 2D and 3D half-Fourier FSE as Arterial Spin Labeling," Proc. Int'l Soc. Mag. Reson. Med. 10, 2002, p. 1.

Amendment Under 37 C.F.R. §1.111 submitted on Apr. 19, 2013 in U.S. Appl. No. 12/923,892, Miyazaki.

Isogai et al., "Non-contrast MRA of the Toes using time-Spatial Labeling Inverse Pulse (time-SLIP) and Optimization of Flow-spoiled Gradient Pulses for the Assessment of Foot Arteries in Flow-spoiled Fresh Blood Imaging (FBI)," Proc. Intl. Soc. Mag. Reson. Med., vol. 16, p. 2901 (2008).

Office Action mailed Jun. 16, 2015 in JP Application No. 2011-226171.

* cited by examiner

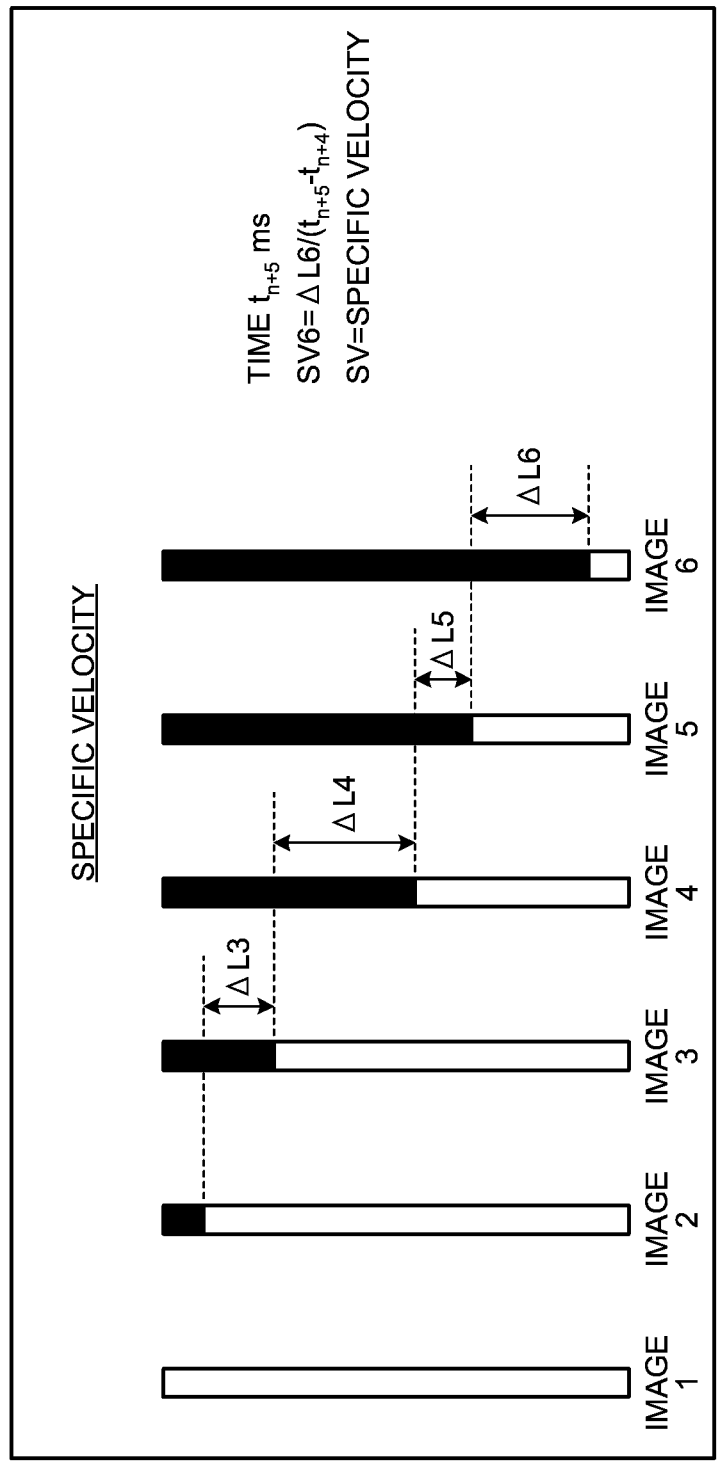

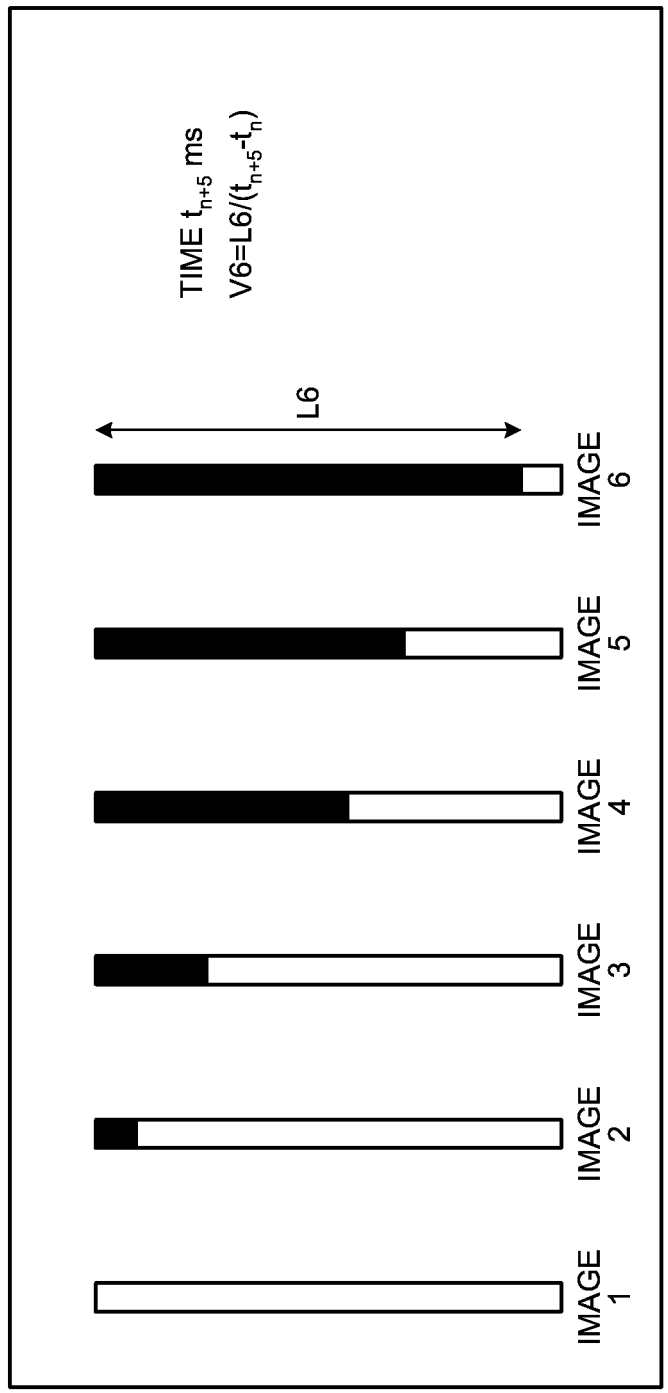

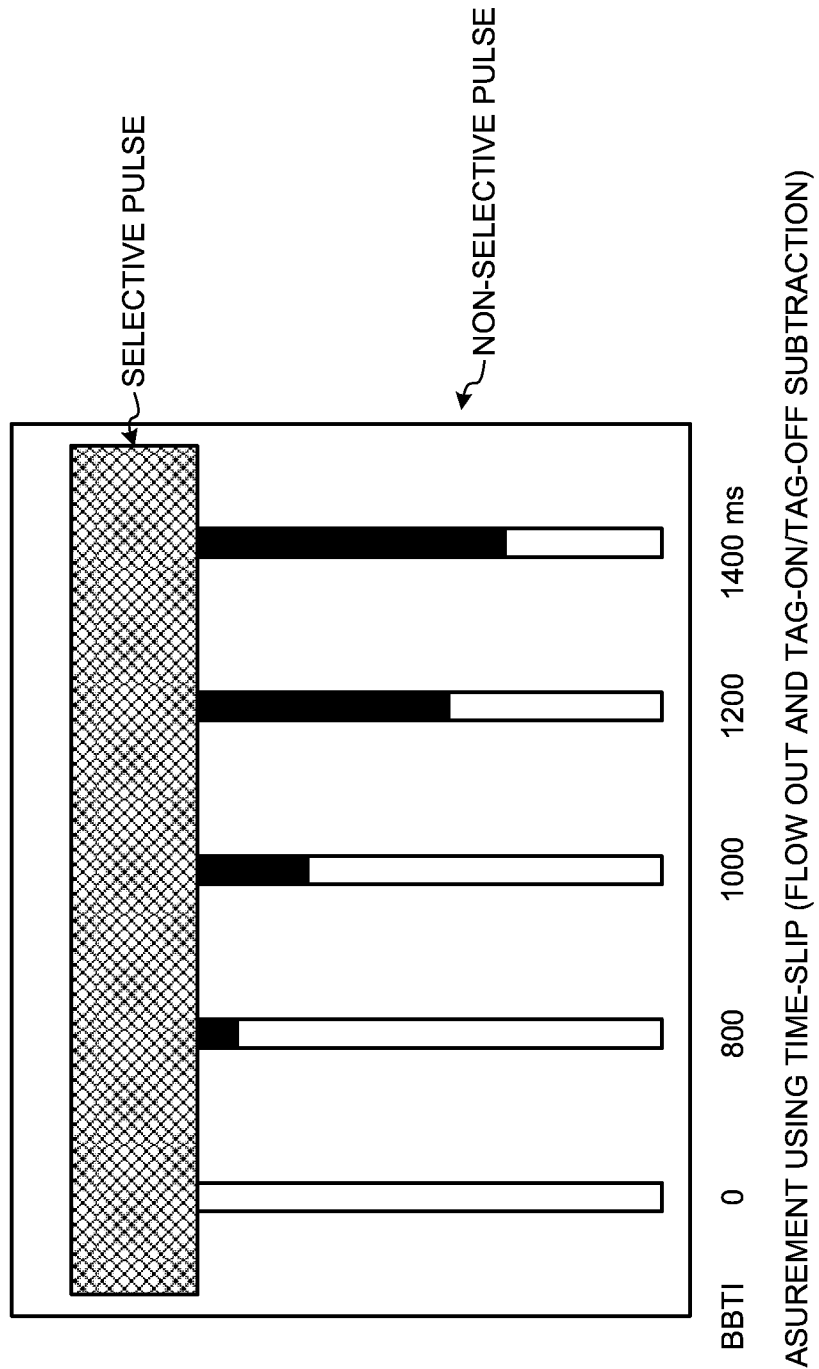

MULTIPLE MR FLUID FLOW IMAGING AT PREDETERMINED TEMPORAL RESOLUTION WITHIN SELECTED PERIOD OF CARDIAC CYCLE DETERMINED BY MULTIPLE MR IMAGING AT DIFFERENT TEMPORAL RESOLUTION

CROSS-REFERENCE TO RELATED APPLICATIONS

This application is a continuation-in-part (CIP) of application Ser. No. 12/923,892 filed Oct. 13, 2010, the entire content of which is hereby incorporated by reference in this application. This application is based upon and claims the benefit of priority from Japanese Patent Application No. 2011-226171, filed on Oct. 13, 2011, the entire contents of all of which is incorporated herein by reference.

FIELD

Exemplary embodiments relate to a magnetic resonance imaging apparatus and a magnetic resonance imaging method.

BACKGROUND

Imaging methods of conventional magnetic resonance imaging apparatuses (hereinafter, MRI (magnetic resonance imaging) system) include a method of imaging a fluid traveling through a subject without using a contrast agent.

BRIEF DESCRIPTION OF THE DRAWINGS

FIG. 10 is a similar schematic diagram showing the images different from those of FIGS. 8 and 9, but now with annotations depicting how a specific velocity can be calculated at each successive period in accordance with an exemplary embodiment;

FIG. 11 is similar to FIG. 10, but now demonstrating how an overall mean or average velocity can be calculated over the entire sequence of difference images in an exemplary embodiment; and FIG. 12 schematically depicts velocity measurements in accordance with another exemplary embodiment using a Time-SLIP (time-spatial labeling inversion pulse) imaging method (flow-out and tag-on/tag-off subtraction methods).

DETAILED DESCRIPTION

A magnetic resonance imaging apparatus according to an exemplary embodiment includes a determining unit and an imaging unit. When a fluid traveling through a subject is imaged for multiple times at different phases, the determining unit determines a period on the time axis within which imaging is performed at intervals satisfying a predetermined temporal resolution. The imaging unit performs imaging for multiple times by the temporal resolution within the period.

Figure 1:
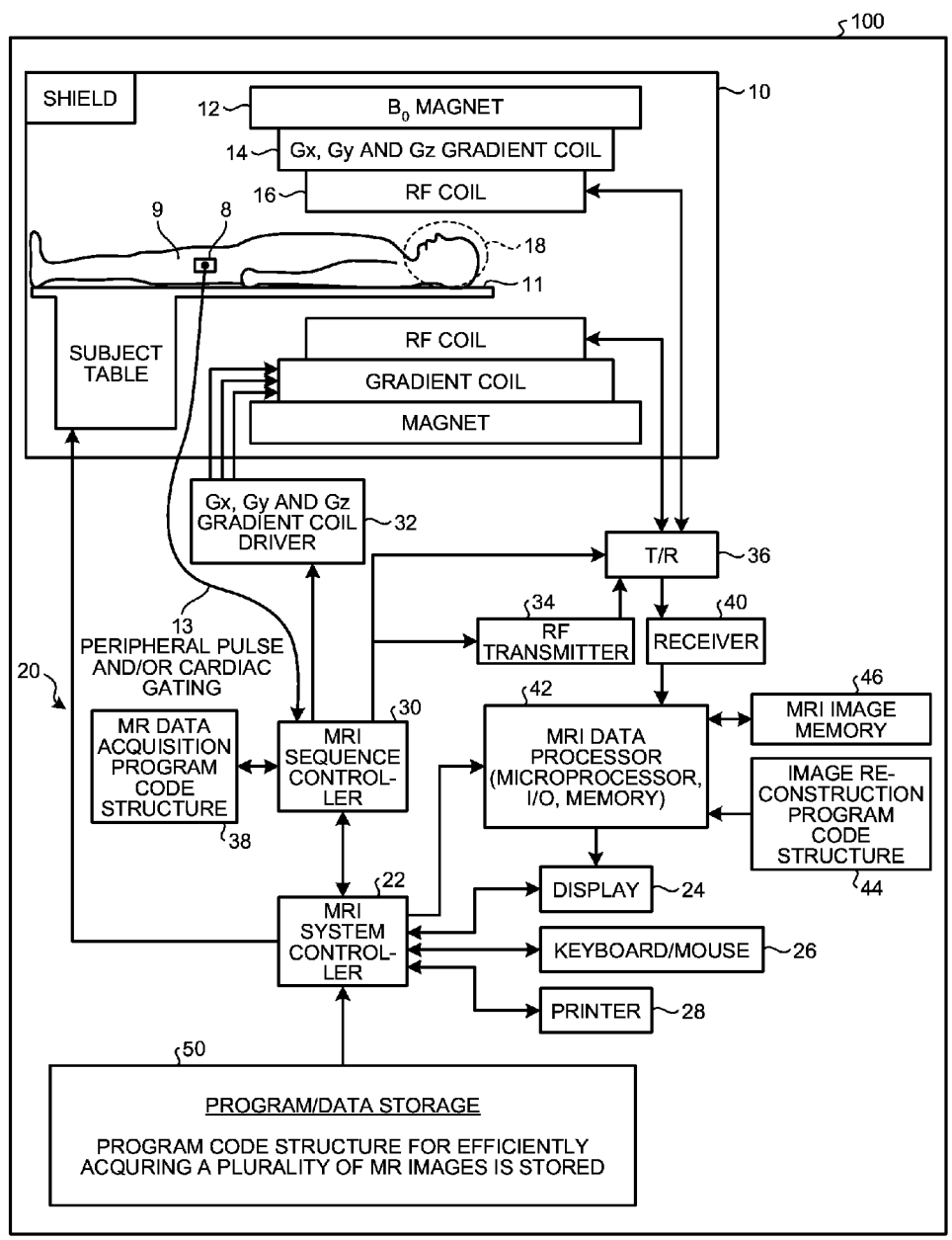
FIG. 1 is a schematic block diagram of an MRI system according to an exemplary embodiment.

An MRI (magnetic resonance imaging) system 100 shown in FIG. 1 includes a gantry 10 (shown in cross-section) and various related system components 20 interfaced therewith. At least the gantry 10 is typically located in a shielded room. One MRI system 100 depicted in FIG. 1 includes a substantially coaxial cylindrical arrangement of a static magnetic field $B_0$ magnet 12, a $G_x$, $G_y$, and $G_z$ gradient coil set 14 and an RF (radio frequency) coil assembly 16. Along the horizontal axis of the components cylindrically arranged, there is an imaging volume 18 shown as encompassing the head of a subject 9 supported by a subject table 11.

An MRI system controller 22 has input/output ports connected to a display 24, a keyboard/mouse 26 and a printer 28. As will be appreciated, the display 24 may be of the touch-screen variety so that it provides control inputs as well.

The MRI system controller 22 interfaces with an MRI sequence controller 30. The MRI sequence controller 30 sequentially controls $G_x$, $G_y$ and $G_z$ gradient coil drivers 32, as well as an RF transmitter 34 and a transmit/receive switch 36 (if the same RF coil is used for both transmission and reception). The MRI sequence controller 30 includes a suitable program code structure 38 for implementing MRI data acquisition sequences available in the MRI sequence controller 30. Cardiac signal acquisition apparatus 8 (positioned as appropriate on the subject anatomy) can output peripheral pulsatile and/or cardiac gating signals 13 to trigger the MRI sequence controller 30.

The MRI system 100 includes an RF receiver 40 providing input to an MRI data processor 42 so as to create processed image data to be output to the display 24. The MRI data processor 42 may be also configured to access an image reconstruction program code structure 44 and an MR image memory 46 (e.g., for storing MRI data derived from processing in accordance with the exemplary embodiments and the image reconstruction program code structure 44).

FIG. 1 also gives a generalized depiction of an MRI system program/data storage 50. The program code structures (e.g., for image reconstruction for, for example, non-contrast MRA (magnetic resonance angiography) and pre-scan systole/diastole determinations within a cardiac cycle, operator inputs, etc.) are stored in computer-readable storage media accessible to the various data processing components of the MRI system 100. As those in the art will appreciate, the program storage 50 may be segmented and directly connected, at least in part, to different ones of the processing computers of the MRI system 100 having most immediate need for such stored program code structures stored in their normal operation (i.e., rather than being commonly stored in and connected directly to the MRI system controller 22).

Indeed, as those in the art will appreciate, the depiction of FIG. 1 is of a very high-level simplified diagram of the typical MRI system 100 with some modifications so as to practice the exemplary embodiments to be described below. The system components can be divided into different logical collections of "boxes" and typically include numerous digital signal processors (DSP (digital signal processors)), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs (central processing unit), registers, buffers, arithmetic units, etc.) progressively change from one clock cycle to another during the operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage in physical storage media will be transformed from some prior state (e.g., all uniform "zero" values or all "one" values) to a new state. In such a new state, the physical states at the physical sites of such an array vary between minimum and maximum values to represent real world physical events and conditions (e.g., the blood flowing in arteries of a subject over an imaging volume space). As those in the art will appreciate, such arrays of stored data values represent and also constitute a physical structure. In other words, when such an array is sequentially loaded into instruction registers and executed by one or more CPUs of the MRI system 100, a particular sequence of operational states occurs and thus a particular structure of computer control program codes that is transitioned through within the MRI system 100 is constituted.

The exemplary embodiments described below provide improved ways to process data acquisitions and/or to generate and display MR-images.

The MRI system 100 according to the exemplary embodiment includes a determining unit and an imaging unit. When a fluid (e.g., blood, CFS (cerebrospinal fluid)) traveling through a subject is imaged for multiple times at different time phases, the determining unit determines a period on the time axis within which imaging is performed at intervals that satisfy a predetermined temporal resolution. The imaging unit performs imaging for multiple times by the predetermined temporal resolution within the determined period. For example, the MRI system controller 22 includes the determining unit and the imaging unit (not shown). The determining unit and the imaging unit are, for example, the MRI sequence controller 30, the gantry 10, and other related components. Some cases will be described below as exemplary embodiments. However, exemplary embodiments are not limited to the following cases.

Case 1 is a case where pre-imaging is performed by a low temporal resolution over the whole period on the time axis and, on the basis of the images collected by the pre-imaging, a period (hereinafter, "interest period" as necessary) is determined within which imaging is performed by a predetermined temporal resolution (a temporal resolution higher than that of the pre-imaging). Case 1-1 is a case using an FBI (fresh blood imaging) imaging method and Case 1-2 is a case using a Time-SLIP (time-spatial labeling inversion pulse) imaging method.

Case 2 is a case where an interest period is determined not on the premise of pre-imaging. Case 2-1 is a case where an interest period is determined by using Auto-ECG (electrocardiogram) to automatically determine an optimum delay from a synchronization signal, and Case 2-2 is a case where an interest period is determined on the basis of a t1 value of a background signal to be controlled.

Each case will be described sequentially.

[Case 1]

Case 1 will be described. First, in Case 1-1, the determining unit performs whole period pre-imaging by ECG-Prep imaging and determines an interest period on the basis of images collected by the pre-imaging. The imaging unit then performs imaging for multiple times satisfying a predetermined time interval (a temporal resolution higher than that of the ECG-prep imaging) by using an FBI imaging method within the determined interest period.

The FBI method is a vessel imaging method by 3D FASE (fast asymmetric spin echo), or an imaging method in which an appropriate delay from a synchronization signal (for example, R wave) is set and, by performing collecting by using electrocardiographic synchronization or pulse synchronization, new blood pumped out of the heart is depicted. The ECG-Prep imaging is 2D FASE imaging that is performed prior to imaging by the FBI imaging method in order to set a delay in the FBI method.

By performing the overall period pre-imaging by ECG-Prep imaging, the determining unit collects a plurality of images at different cardiac phases while changing the delay from the synchronization signal (e.g., R wave). At that time, the determining unit performs imaging by a temporal resolution lower than that of the following imaging. In addition, the determining unit displays on a display the collected images or a transition of the signal value analyzed on the basis of the images. For example, the determining unit extracts an area in which the signal value significantly changes by analyzing the images collected by ECG-Prep imaging, obtains signal value differences each between a reference image and each image, and displays the obtained signal value differences in a graph (for example, this feature is referred to as "FBI-Navi" as necessary below).

The determining unit then determines an interest period by accepting specifying by the operator for the images and the transition of signal value displayed on the display. For example, the operator browses the images and the transition of the signal value displayed on the display and specifies, for example, a period within which the intensity of an MR signal rapidly changes from systole to diastole. The determining unit may display images corresponding to the period specified by the operator on the display. This allows the operator to identify to what extent the fluid is depicted in accordance with the specified delay. The determining unit may automatically determine an interest period from the transition of the signal value analyzed on the basis of the images collected by ECG-Prep imaging.

The imaging unit then performs imaging for multiples times at intervals that satisfy a predetermined temporal resolution (a temporal resolution higher than that of ECG-Prep imaging) by using the FBI imaging method within the determined interest period. The MRI system 100 may further include a play controller that successively plays the images in time series collected by the imaging by the imaging unit for multiple times. For example, the play controller may generate difference images between each image collected at a predetermined cardiac phase and an image collected at a reference cardiac phase and successively plays the generated difference images. Video images of the flowing fluid are displayed.

In Case 1-2, the determining unit performs whole period pre-imaging by BBTI (black-blood time to inversion)-Prep imaging and determines an interest period on the basis of the images collected by the pre-imaging. The imaging unit then performs imaging for multiple times, which satisfies a predetermined time interval (temporal resolution higher than that of BBTI-Prep imaging), within the determined interest period by using a Time-SLIP (time-spatial labeling inversion pulse) imaging method.

The Time-SLIP imaging method is an imaging method of depicting a fluid flowing into or flowing out of an imaging area by labeling (tag-on) the fluid in positions independent of the imaging area and increasing or reducing the signal value of the fluid flowing into or flowing out of the imaging area. In the Time-SLIP imaging method, a Time-SLIP pulses are applied after a predetermined wait time from the synchronization signal (e.g., R wave). The Time-SLIP pulses include an area non-selective inversion pulse and an area selective inversion pulse and on or off can be set for the area non-selective inversion pulse. When the fluid flowing into (or flowing out of) the imaging area is labeled by using the area selective inversion pulse, the intensity of the signal of the part that the fluid has reached after BBTI time increases (decreases when the area non-selective inversion pulse is off).

When a labeling position is set outside the imaging area, the labeled fluid flows into the imaging area, which is referred to as "flow-in". In contrast, when a labeling position is set within the imaging area, the labeled fluid flows out of the imaging area, which is referred to as "flow-out". The exemplary embodiments can be applied to both "flow-in" and "flow-out". It is satisfactory if two fluid images are collected by alternately repeating collecting in which labeling by using an area selective inversion pulse is performed and collecting in which labeling by using an area selective inversion pulse is not performed and only the labeled part is extracted by using a difference image between the collected two images to reduce the background signal. Furthermore, the labeling method is not limited to the above-describe method and, as an application, pCASL (pulsed continuous arterial spin labeling) method of successively radiating labeling pulses may be used.

Furthermore, BBTI-Prep imaging is imaging by using the Time-SLIP imaging method with 2D FASE that is performed prior to the imaging by using the Time-SLIP imaging method in order to set a BBTI time in the Time-SLIP imaging method. The determining unit collects a plurality of images at different phases while changing the BBTI time from the synchronization signal by performing the whole period pre-imaging by BBTI-Prep imaging. At that time, the determining unit performs imaging by a temporal resolution lower than that of the following imaging. The determining unit displays on the display the collected images or a transition of the signal value analyzed on the basis of the images. For example, the determining unit analyzes a background signal from the images, which are collected by BBTI-Prep imaging, and displays the obtained signal values in a graph.

Subsequently, the determining unit determines an interest period by accepting specifying by the operator for the images and the transition of the signal value displayed on the display. For example, the operator browses the images and the transition of the signal value displayed on the display and, for example, specifies a period in a predetermined range before and after the time where the signal value of the background signal is "0". The determining unit may display on the display images corresponding to the period specified by the operator. This allows the operator to identify to what extent the fluid is depicted in accordance with the specified delay. The determining unit may automatically determine an interest period from the transition of the signal value analyzed on the basis of the images collected by BBTI-Prep imaging.

The imaging unit then performs imaging for multiples times at intervals that satisfy a predetermined temporal resolution (a temporal resolution higher than that of BBTI-Prep imaging) by using the Time-SLIP imaging method within the determined interest period. The MRI system 100 may further include a play controller that successively plays the images, which are collected by the imaging by the imaging unit for multiple times, in time series. For example, the play controller may generate, at each phase, a difference image between two images collected at the same phase by repeating collecting in which labeling is performed and collecting in which labeling is not performed and successively play each of the generated difference images.

Case 1-1 and Case 1-2 will be described in detail below using specific examples.

In time-resolved non-contrast MRA (magnetic resonance angiography), an image can be obtained by successively acquiring MR images at small incremental delay times (repeat) throughout the R-R cycle so as to surely include systole to diastole and the subtraction of dark (with low signal intensity) signals at systole from the bright signals (with high signal intensity) at or during diastole. In this method, one or more images of blood travel between systole and diastole in the cardiac cycle.

However, one does not initially know where the appropriate sub-period or sub-interval (interest period) of a cardiac cycle resides in the PQRSTU. Thus, all data is acquired with small increments of delay to acquire finely separated data acquisition sequences over a whole cardiac R-R period and then the most suitable images at (a) diastole and (b) systole are found to subtract and produce the time-resolved fluid vascular image (e.g., MRA image).

To reduce wasted resource usage, the exemplary embodiment (for example, the above-described Case 1-1) first performs an ECG-Prep rough scan with relatively large rough increments (e.g., 100 ms) to cover a whole cardiac cycle. Furthermore, the MRI system 100 uses FBI-Navi or some similar programs to display a graph of the rough signal intensity versus delay time to allow operator selection of the beginning and the end of steep signal changes and a finer increment that the operator can select. Furthermore, the MRI system 100 can automatically calculate the final scan repeat interval (i.e., how many times to repeat a scan within the defined interest period). For example, as described in the following Case 2, an Auto-ECG mode as described in commonly assigned application Ser. No. 12/699,169 may be employed to use the heart rate in order to calculate systole and diastole and to determine systolic and diastolic delays.

The MRI system 100 automatically subtracts signals from the "black (with low intensity)" systolic image from the "bright (with high intensity)" diastolic image (or vice versa) to display time-resolved images (2D and 3D). In a cine mode, the MRI system 100 can show a sequence of such images in flow-like hemodynamic moving images. Similarly, as in the above-described Case 1-2, as for time-resolved images collected by using the Time-SLIP method, the MRI system 100 can display an FBI-Navi-like plot (graph) of 2D BBTI-prep imaging results and an operator may select a desired period parameters and/or repeat parameters for the data acquisition in 2D and/or 3D.

Time-resolved non-contrast images can be obtained using a signal acquisition duration during a relevant signal changing area (which alternatively can be automatically selected by the system to encompass detected steep slope periods instead of relying upon an operator's selection).

An GUI (graphical user interface) of the above interface and system scan operation and subtraction can produce flow-like images while allowing a reduction of scan time to obtain time-resolved non-contrast images in FBI and Time-SLIP imaging.

Because one does not initially know when particular signal intensity changes occur within a cardiac cycle, multiple scans with a small increment (for example, 10 ms) have been used to cover a whole cardiac cycle. For example, when an interval of 10 ms is used, an R-R cycle of 1,000 ms requires 100 MRI data acquisition sequences. In order to collect 3D data (2D spatial data with 1D in time) by using a 3RR cycle per scan, 2D scan takes 3RR×100=300RRs or 300 cardiac beats. 300× 1000 ms=300 sec or 5 minutes. In order to collect 4D data (3D spatial data with 1D in time), it may thus take 50 minutes for 10 slices. In addition, the post-acquisition processing of those extensive acquired data sets takes a long time (e.g., due to not initially knowing where the diastolic or high intensity signal is to be found for subtraction and where the lowest or peak systolic phase can be found).

Figure 2:
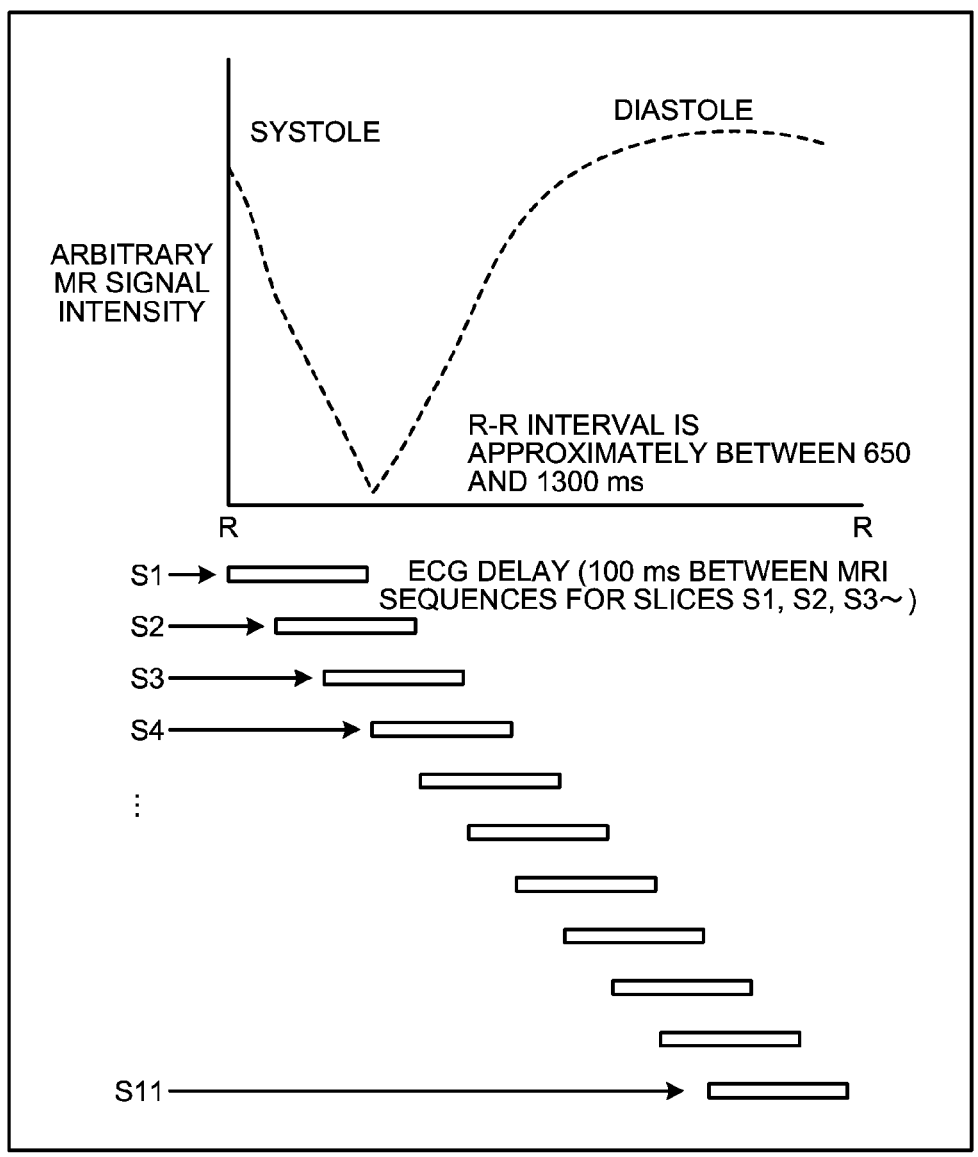
FIG. 2 is a schematic diagram showing MR signal intensity over a cardiac-cycle R-R interval as measured roughly by a succession of successively delayed MRI slice imaging sequences in an exemplary embodiment so as to quickly identify a desired sub-period (e.g., a systole/diastole period)
Figure 3:
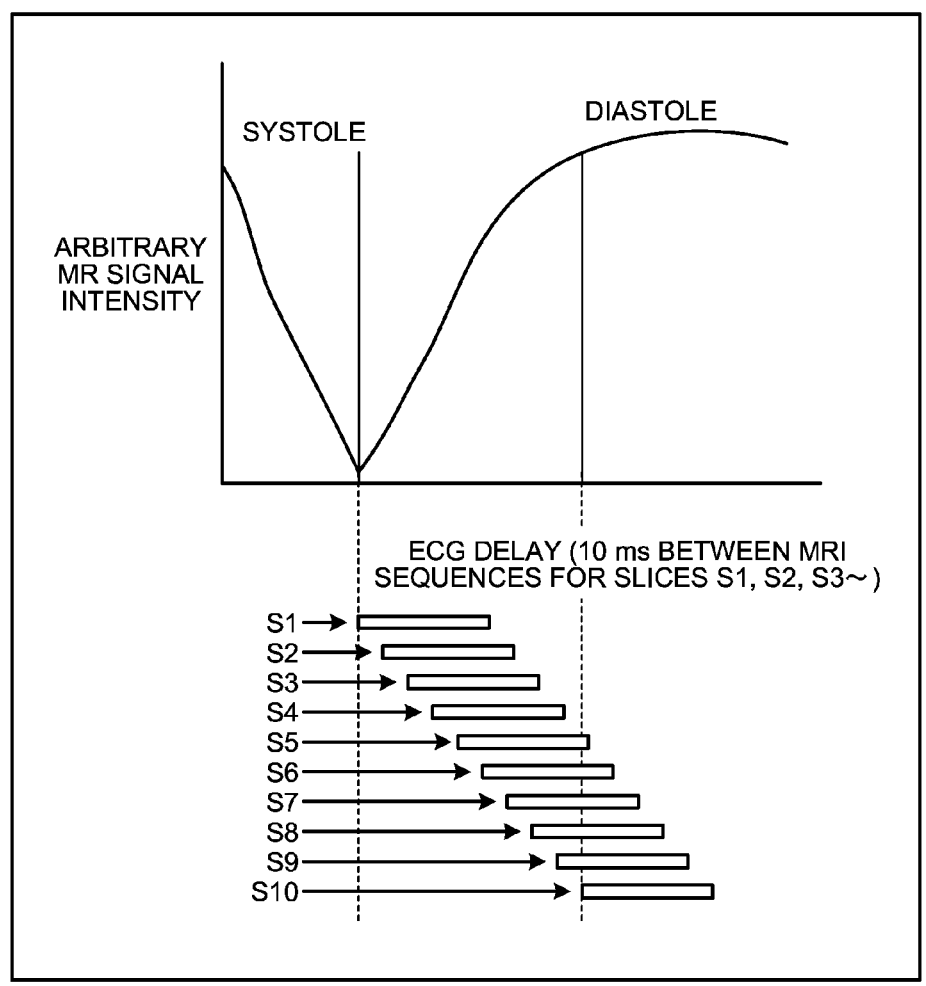
FIG. 3 is similar to FIG. 2, but now accomplished using a fewer number of but more closely spaced (in time) MRI slice imaging sequences depicted within the shorter systole/diastole period identified using the rough scan of FIG. 2.
Figure 5:
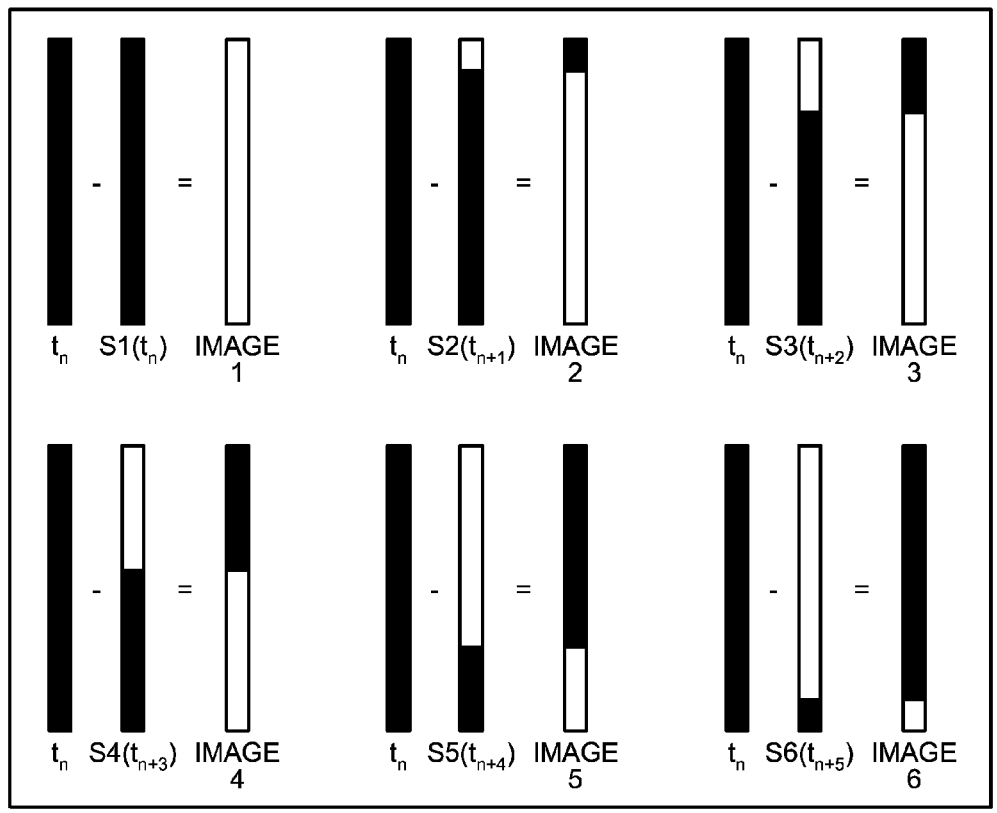
FIG. 5 is a schematic diagram of a succession of difference images that can be obtained by subtracting a "dark (with low signal intensity)" base systolic image and each of a succession of "brighter (with high signal intensity)" images on a pixel-by-pixel basis as the MRI data acquisition sequence is moved towards diastole.
Figure 6:
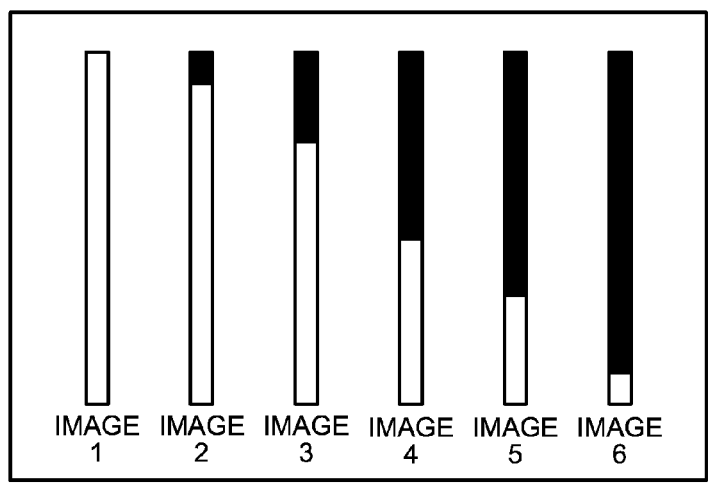
FIG. 6 is an extract showing Images 1 to 6 derived from FIG. 5.

As noted above, typically, one does not know the signal intensity curve for a particular subject in advance. Thus, a whole cardiac cycle of consecutively delayed slice images is acquired using single shot FSE (FASE) or any other suitable MRA sequences (EPI (echo planar imaging), bSSFP (balanced steady state free precession), etc.) with a small increment like 10-20 msec. Now, however, in order to initially ascertain a rough signal intensity curve, the MRI system 100 can use an ECG-prep scan using a relatively large increment (roughly like 100 ms) to cover a whole cardiac cycle, as shown in FIG. 2. By using an FBI-Navi (a plot of signal intensity versus ECG time), the MRI system 100 can select a desired shorter increment and start and end times (i.e., interest period) and a desired shorter increment for the consecutively delayed MRI sequences as shown in FIG. 3. Subtraction of lower intensity signals in systole from higher intensity signals of images depicted in diastole will give time-resolved MRA images visually representing traveling blood signals, as shown in FIG. 5. Note that S1, S2, . . . Sn are systolic phases 1, 2, . . . n. If displayed in cine mode (FIG. 6), non-contrast time-resolved MRA can be seen.

Acquiring only the steep signal changing from systole to diastole with the smaller delay increment allows an overall faster scan time for time-resolved non-contrast MRA. Further shortening of scan time can be made. Shortening of scan time can be made by using the follows.

T2 plus (90 degree reverse pulse at the end of the data acquisition to bring the x-y magnetization to the +z direction)

Higher parallel imaging factor to shorten an actual single shot time and reducing the TR (repetition time) from 3RR interval to 1 or 2RR interval A keyhole scan to share the peripheral k-space data using a full sample at the diastole (or systole) and a center part of k-space to acquire and share the non-acquired part (elsewhere than a center) to make images.

This shortens the scan time to obtain a non-contrast time-resolved in 2D spatial with 1D time images or 3D spatial with 1D time images. An easy-to-use GUI can be provided for this time-resolved technique using the systolic to diastolic period by selecting the start and end of the scan cycle and by presetting the delay increment (e.g., by having the system calculate a repeat increment).

Non-contrast time-resolved images (2D spatial+1D time=3D or 3D+1D time=4D) imaging can be obtained using this type of ECG-Prep imaging or FBI-Navi result. Without this approach, it takes a long time to acquire a single shot FSE image at a small repeat increment over the whole cardiac cycle. Now, the result of the initial rough FBI-Navi can be used to select the start and end of scan(s) and, if desired, a delay increment to cover the low intensity signal (systolic) to high intensity signal (diastolic) triggering times. The system may automatically calculate the repeat interval, acquire multiple scans in different phases (2D or 3D scans) and subtract the systolic data from diastolic data (or vice versa) to display time-resolved MR images as flow dynamics.

This approach can provide time-resolved non-contrast images obtained using FBI-Navi, selection of duration (interest period) (signal change area, which can be automatically selected by the system (steep slope detection) or selected by the operator). A friendly GUI of the above interface, system scan operation and subtraction can produce flow-like images.

In the exemplary embodiments, since the curve representing MR signal intensity versus time throughout an R-R interval of the cardiac cycle for a particular subject is not known in advance, a rough scan of the interval for a given subject may be utilized to quickly discern the location of systole and diastole timings. For example, as shown in FIG. 2, a succession of MRI slice imaging sequences S1, S2 . . . may be effected at relatively large intervals (e.g., 100 msec or so) over the R-R interval for that given subject (which may approximate 650 to 1,300 msec or so). In this manner, the MR signal intensity over the R-R cycle is initially depicted as depicted in FIG. 2 so as to identify the timing of minimum MR signal intensity (systole) and the timing of maximum MR signal intensity (diastole).

Once the systole and diastole time points have been identified for that particular subject, then a more concentrated (i.e., more closely spaced in time) series of successively delayed MRI slice imaging sequences may be effected so as to capture the most desirable part of the R-R cycle, namely, between systole and diastole as depicted in FIG. 3. Here, the MRI sequences may be more closely spaced (e.g., 10 msec or so) so as to obtain the desired level of incremental change between images. This allows the use of techniques such as FBI-Navi in 2D and/or 3D acquisitions as time-resolved non-contrast MRA images. When these successive images are displayed in cine mode, they appear as a hemodynamic display of blood flowing through vessels (or other fluids flowing through other appropriate vessels) within the imaged subject. However, by first doing an initial rough scan as in FIG. 2 in order to depict the MR signal intensity curve during an R-R interval for a given subject and then concentrating only on the desired (e.g., systole/diastole) part of that curve for the more finely closely separated series of images, a considerable amount of time can be saved.

Figure 4:
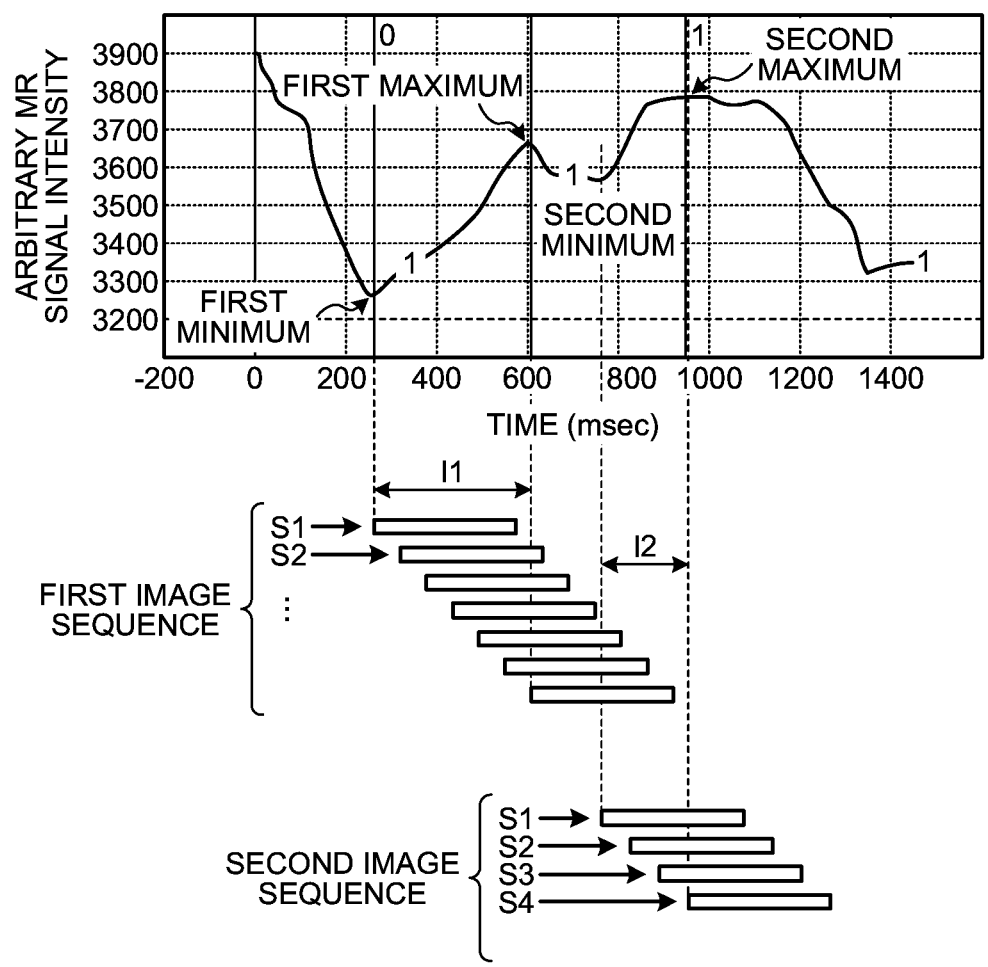
FIG. 4 is similar to FIG. 3, but illustrates the possibility of capturing a plurality of signal periods (relatively positively-sloped signal periods) that may be separated from one another within the systole/diastole period.

As depicted in FIG. 4, some subjects may have an MR signal intensity curve that has more than two or more pairs of minimum and maximum points. As shown in FIG. 4, for example, first minimum and first maximum systole/diastole points define a first period I1 with most of the positively sloped intensity curve for which a first sequence of images is then captured. However, in addition, this particular subject exhibits a second period I2 with second minimum and second maximum points. Accordingly, this second smaller period defining a second smaller positively sloped region can also be captured in a second sequence of consecutively delayed slice imaging MRI sequences as also depicted in FIG. 4. In effect, this permits the capturing of positively sloped portions of the intensity curve that occur in later time segments.

FIG. 5 schematically depicts idealized sections of a linear artery that is imaged at various timings and then subtracted (e.g., diastole-systole) to produce a series of images that can be displayed in cine mode (e.g., see FIG. 6) to simulate a video display showing a volume of blood traveling through that imaged section of artery. While this type of FBI-Navi display is, of course, known in the prior art, the use of an initial rough, longer interval, and mapping sequence as in FIG. 2 so as to permit restriction of the closer spaced successive images more precisely in a thusly identified systole/diastole interval as shown in FIGS. 3 and 4 greatly decreases the overall data acquisition time.

Changes in arterial signal intensity can be drastic from end systole to early diastole. However, each subject has a different timing for this change. In order to find the most relevant time period when there is increasing signal intensity, FBI-Navi can be used to determine a rough estimation of systolic and diastolic triggering times (e.g., as acquired using an ECG-Prep imaging, single slice with multiple phases).

In order to reduce total acquisition time for time-resolved non-contrast MRA, if the result of the FBI-Navi and time-resolved images is used, more effective acquisition can be made in the period of drastically increasing signal change from late systole to early diastole.

To efficiently obtain time-resolved non-contrast MRA images, a drastically increasing signal change period from late systole to early diastole can be automatically determined using the FBI-Navi, as shown in FIG. 2. Thereafter, the system can automatically determine the optimum scan period. An operator can selectively determine the incremental delay and/or the system can calculate a suitable repeat time to acquire successively delayed slice images throughout the systole to diastole period. The system may then subtract each of the successive systolic images from the diastolic depicted image (high intensity signal) and can display the succession of subtracted images.

The desired signal change period (e.g., late systole to early diastole) as measured using FBI-Navi can then be acquired with a smaller delay increment. Alternatively, as described in the following Case 2, signal change period calculated by Auto-ECG (e.g., see co-pending application Ser. No. 12/699,169) can be used with a smaller increment. Auto-ECG uses heart rate and the measured systolic and diastolic period to calculate a suitable delay interval. Auto-ECG can also automatically determine systolic and diastolic triggering delays.

The MRI system 100 also may automatically determine only the systole/diastole period and let the operator decide upon a desired incremental delay or suggested increment (e.g., 10-20 ms). The MRI system 100 may then calculate an appropriate repeat time to acquire successive images through the relevant period. The MRI system 100 then subtracts the systolic images from the diastolic triggered image (high intensity signal) and displays the subtracted images.

As described in the following Case 2, Auto-ECG may use heart rate and the systolic and diastolic period to determine systolic and diastolic triggering delays.

Time-resolved non-contrast MRA data can thus be acquired in a shorter time. The acquisition period can be selected in an easier manner and data processing such as subtraction, which is cumbersome to do manually, can be done in the system. The system display can be done without manual display in a cine mode.

Figure 7:
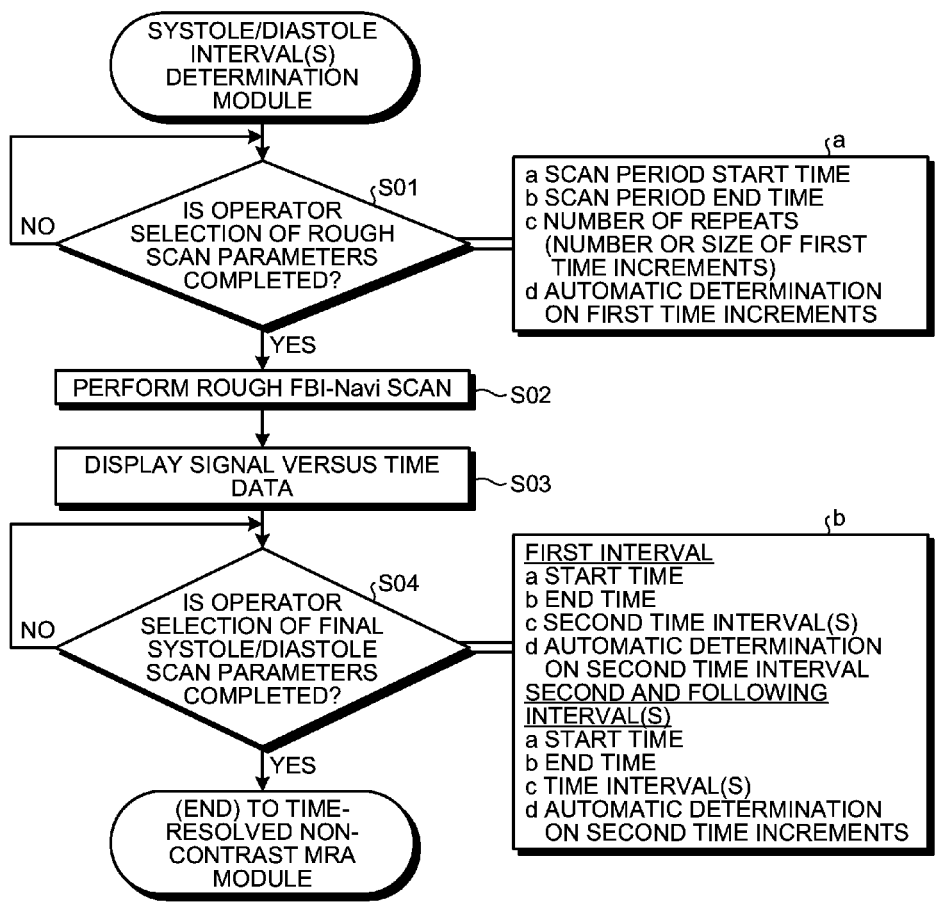
FIG. 7 is a schematic flow chart of an exemplary computer program code structure that may be utilized for practicing an exemplary embodiment.

Exemplary program code structure for a systole/diastole interest period determination module is depicted at FIG. 7.

There, the module is started (e.g., via a suitable operator and/or system command associated with a desire to acquire/display time-resolved MRA images). At step S01, a wait loop is started for operator selection of rough scan parameters. The operator selections may encompass, for example, items such as shown in box a. In box a, the operator may define scan period start and stop times (e.g., R-R interval), the number of repeats or size of delay increments or the like (or may simply let the system automatically determine these first rough scan parameters). Once operator inputs are completed, then a rough FBI-Navi scan (ECG-Prep imaging) is performed at step S02. If further operator inputs are to be permitted (i.e., if fully automatic system operation is not desired), then the created rough scan signal versus time data may be displayed at step S03. Thereafter, a wait loop is started at step S04 and thus the operator can select the final systole/diastole scan parameters. As depicted in box b, such operator selections may include selections for multiple intervals. However, for at least the first interval, the operator may enter scan start and stop times, as well as second smaller time intervals. Alternatively, a selection can be made to let the system automatically determine suitable smaller time intervals for the subsequent time-resolved MRA scanning process.

Once final operator inputs have been completed, then control is passed to the end for time-resolved non-contrast MRA processes conducted in accordance with those operator-set parameters (e.g., as may be accomplished by exit to a separate module where conventional time-resolved non-contrast MRA is performed within the more limited systole/diastole period(s) as determined by the rough scan processes described in the earlier portions of FIG. 7.)

Of course, those in the art will appreciate that, if desired, substantially all of the processes set forth in FIG. 7 could be programmed for automatic implementation by the system without repetition of control inputs by the operator. For example, the operator inputs, if any, could be limited to the pre-setting of basic setting parameters or the like in an overall module for time-resolved non-contrast MRA.

[Case 2]

Case 2 will be described. In Case 2-1, first, the determining unit determines an interest period by using the Auto-ECG imaging method to automatically determine an optimum delay from a synchronization signal. For example, the determining unit collects cardiac phase information (for example, electrocardiogram) from the cardiac signal acquisition apparatus 8 attached to the subject, specifies systole and diastole by analyzing the collected cardiac phase information, and automatically determines, as an interest period, a period in which the signal value rapidly changes from systole to diastole.

In case 2-2, the determining unit determines an interest period on the basis of a t1 value to be controlled. The approximate range of the t1 value of each tissue is previously known and it is known with which exponential function the t1 value of each tissue changes depending on pulse sequence conditions. For example, in the FBI imaging method described in Case 1-1, because difference images between diastolic images and systolic images are usually used, the background signal is subtracted and thus it is less likely that reduction of the background signal is problematic. On the other hand, in the Time-SLIP imaging method described in Case 1-2, difference images are not necessarily used and thus reduction of a background signal may be desired.

The t1 value of the background signal excited by a Time-SLIP pulses changes on the exponential function and there is a null point where the t1 value becomes "0" in the changing process. The period in the predetermined range before and after the null point can be referred to as a sweet spot period in which the background signal is reduced and a preferable signal is depicted as emphasized. Thus, for example, if the tissue of a background signal to be reduced is previously known, the determining unit previously specifies on which exponential function the t1 value of the tissue changes. The determining unit then determines an interest period that satisfies a predetermined temporal resolution by specifying a null point on the exponential function and specifying a sweet spot period.

[Other Cases]

Other cases will be described. Over the whole period covering an interest period, the determining unit performs pre-imaging for multiple times at intervals by a low temporal resolution below a predetermined temporal resolution, calculates a flow velocity of a fluid on the basis of a plurality of images collected by the pre-imaging, and determines an interest period from the calculated flow velocity. More specifically, the determining unit specifies the distance travelled by the fluid by using the images collected by the pre-imaging as well as acquires an elapsed time corresponding to the specified traveled distance from pulse sequence information used for the pre-imaging and calculates a flow velocity of the fluid by dividing the traveled distance by the elapsed time. The determining unit then determines an interest period on the basis of the calculated flow velocity. For example, the determining unit automatically determines, as an interest period, a period on the time axis where there is a predetermined flow velocity or faster. In addition, for example, the determining unit displays a graph representing flow velocity changes on the display and accepts specifying of an interest period by the operator.

A flow velocity calculating process performed by the determining unit will be described in detail below. For example, as in Case 1-1, the determining unit collects a plurality of images at different cardiac phases while changing a delay from a synchronization signal (e.g., R wave) by ECG-Prep imaging. The determining unit then specifies, for each image at a different cardiac phase, a distance traveled by a fluid by using difference images between images collected at predetermined cardiac phases and an image collected at a reference cardiac phase.

Figure 8:
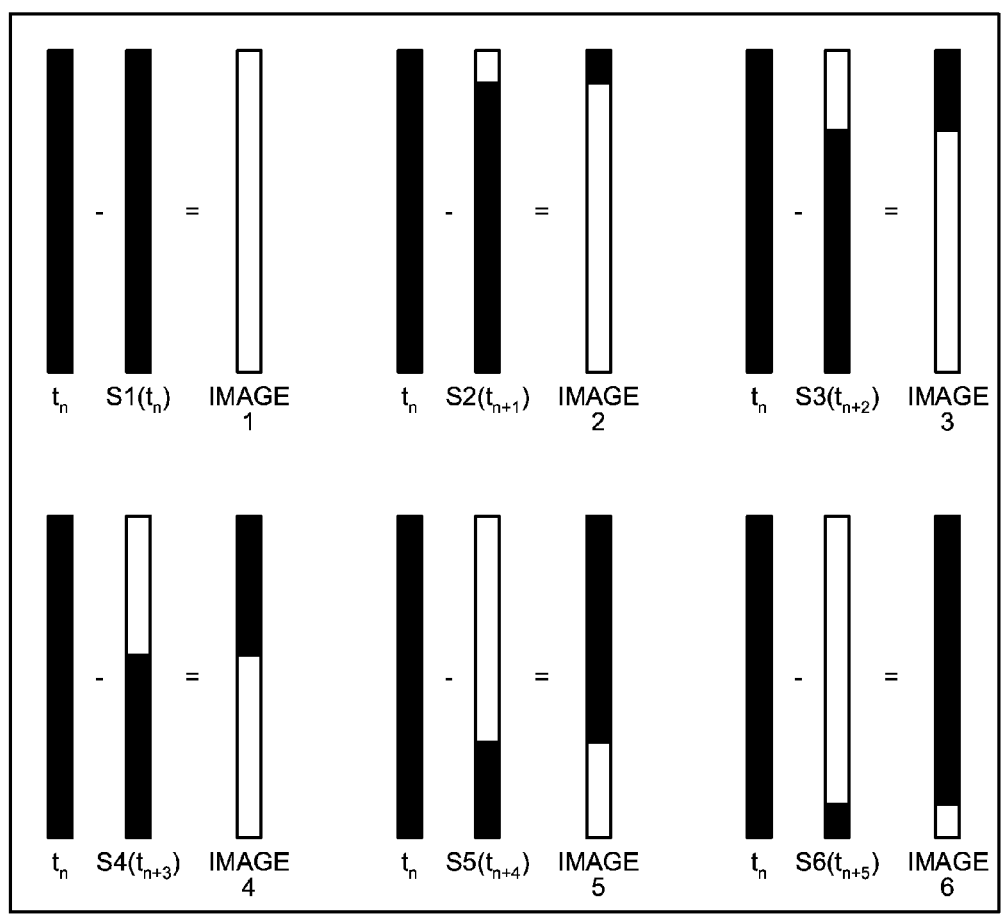
FIG. 8 is a schematic diagram depicting successive difference images obtained by the differences between a "dark (with low signal intensity)" systolic image and "bright (with high signal intensity)" diastolic images at successive cardiac-gated time increments.
Figure 9:
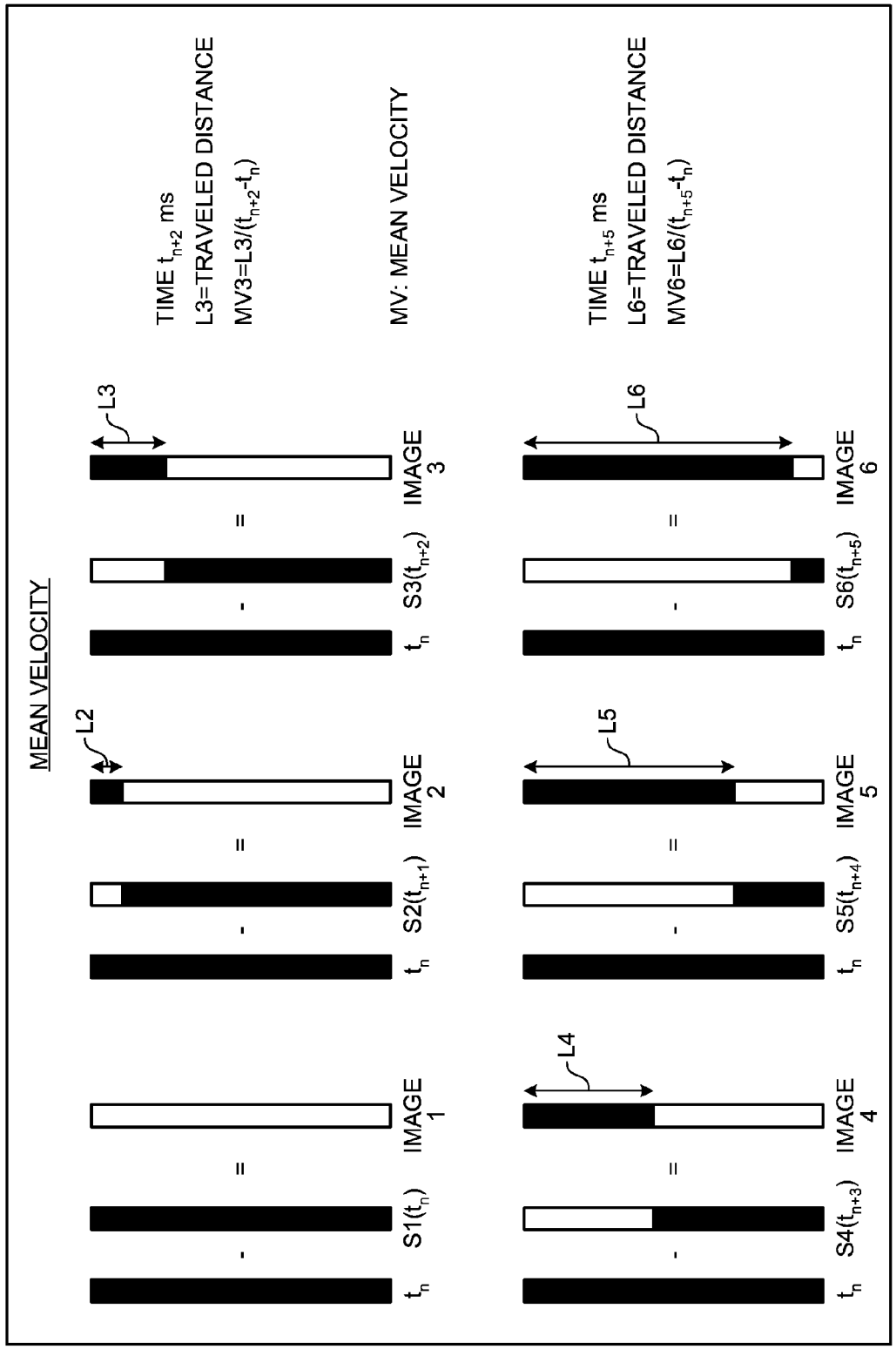
FIG. 9 is a schematic diagram similar to that of FIG. 8, but including annotations explaining how average or mean blood flow velocity can be calculated in accordance with an exemplary embodiment.

As described above, the intensity of the MR signal is different between images at different cardiac phases. For this reason, for example, by subtracting an image collected at a predetermined cardiac phase from the image collected at the reference cardiac phase, a signal of the fluid (e.g., blood) traveling through during that time can be depicted. For example, in FIG. 8, "t," denotes a reference cardiac phase and "S1($t_n$)" denotes the MR signal collected at the cardiac phase $t_n$. As shown in FIG. 8, for example, because the MR signal of the blood pumped out of the heart during systole has a low intensity (expressed by, for example, white in FIG. 8), the low-intensity portion gradually increases as the delay increases. Images 1 to 6 are images, each of which is obtained by subtracting a fluid image at each phase from the fluid image at the reference cardiac phase and subtracting information excluding blood, and each of which depicts only blood. The determining unit specifies a distance traveled by the fluid at each cardiac phase by analyzing Images 1 to 6, which are difference images, and by discriminating, for example, the high-intensity part and the low-intensity part from each other. For example, the determining unit specifies the traveled distances L2 to L6 as shown in FIG. 9.

The determining unit acquires an elapsed time from the pulse sequence information for each traveled distance in each fluid image. For example, in Case 1, the elapsed time corresponding to each cardiac phase corresponds to a delay that is set as pulse sequence information. For this reason, the determining unit acquires the delay that is set as the pulse sequence information. For example, the determining unit acquires $t_{n+1}$ msec, $t_{n+2}$ msec, $t_{n+3}$ msec, $t_{n+4}$ msec and $t_{n+5}$ msec as shown in FIG. 9.

The determining unit calculates a flow velocity by using each traveled distance and each elapsed time. For example, the determining unit calculates a specific velocity for the cardiac phase by dividing a certain traveled distance by an elapsed time corresponding to the traveled distance. For example, as shown in FIG. 9, the determining unit calculates a mean velocity MV3 by dividing a traveled distance L3 by an elapsed time ($t_{n+2}-t_n$). The method of calculating a velocity is not limited to this. As shown in FIG. 10, the determining unit may calculate a specific velocity SV by dividing a traveled distance ΔL6 of a difference between Image 6 and Image 5 by an elapsed time ($t_{n+5}-t_{n+4}$). Alternatively, for example, as shown in FIG. 11, a velocity may be calculated by dividing an accumulated traveled distance L6 obtained by accumulating at each cardiac phase by an accumulated traveled distance ($t_{n+5}-t_n$).

Subsequently, other examples will be described. For example, as in Case 1-2, the determining unit collects a plurality of images at different phases while changing the BBTI time from a synchronization signal (e.g., R wave) by BBTI-Prep imaging. The determining unit then specifies a traveled distance of the fluid for each image at a different phase.

As shown in FIG. 12, the high-intensity part increases gradually as the BBTI time increases (expressed by, for example, black in FIG. 12). For example, the determining unit specifies a distance traveled by the fluid at each phase by analyzing each image on the basis of the intensity and, by discriminating, for example, the high-intensity part and the low-intensity part from each other. If two images are collected by alternately repeating collecting in which labeling is performed and collecting in which labeling is not performed at the same phases, the determining unit extracts only a labeled part by using a difference image between the collected two images and specifies a traveled distance of a fluid for each image at a different phase.

The determining unit acquires an elapsed time for each traveled distance in each image from pulse sequence information. For example, a case is assumed where the determining unit collects a plurality of images at different phases by using the Time-SLIP imaging method using the FASE method. In this case, the determining unit acquires, as an elapsed time, a value obtained by adding a BBTI time to an TEeff (effective time to echo) from the pulse sequence information. In addition, a case is assumed where the determining unit collects a plurality of images at different phases by using the Time-SLIP imaging method using a bSSFP (balanced steady state free precession) method. In this case, the determining unit acquires, as an elapsed time, a BBTI time from the pulse sequence information in centric ordering in which phase encodes are arrayed from the center of the k space. In contrast, in sequential ordering in which phase encodes are sequentially arrayed in the k space, the determining unit acquires, as an elapsed time, a value obtained by adding a BBTI time to a time corresponding to half of the phase encode number. These elapsed times are designed to correspond to the elapsed times in which MR signals with which the center part of the k space is filled are collected.

Furthermore, as applications, a pCASL (pulsed continuous arterial spin labeling) method in which labeling pulses are successively radiated may be used as a labeling method.

According to the magnetic resonance imaging apparatus and magnetic resonance imaging method according to at least one of the above-described exemplary embodiments, a fluid can be imaged efficiently.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a determining unit configured to, when a fluid traveling through a subject has been imaged for multiple times at different phases of the subject's cardiac cycle at a first temporal resolution and the different phases cover a first period of the cardiac cycle, determine a second period of the cardiac cycle on a time axis within which further imaging of the fluid is to be performed at intervals satisfying a second temporal resolution; and
an imaging unit configured to perform imaging of the fluid for multiple times at the second temporal resolution within the second period,
wherein the imaging unit performs imaging multiple times within the first period at the first temporal resolution being below the second temporal resolution and the determining unit determines, on the basis of a plurality of images collected at the first temporal resolution, the second period being included in the first period.

2. The magnetic resonance imaging apparatus according to claim 1, further comprising:
a play controller configured to successively play images, which are collected by the imaging unit for multiple times, in time series.

3. The magnetic resonance imaging apparatus according to claim 1, wherein:
the determining unit:
performs ECG-Prep imaging multiple times to collect a plurality of images at the different cardiac phases while changing a delay time from a synchronization signal,
displays on a display the images collected by the ECG-Prep imaging or a transition of a signal value analyzed on the basis of the images, and
determines the second period by accepting an operator specification, based on the display, of a period that is set between systole and diastole, and the imaging unit:
performs, within the second period, imaging for multiple times at the intervals satisfying the second temporal resolution by using an FBI (fresh blood imaging) imaging method to depict blood pumped out of a heart.

4. The magnetic resonance imaging apparatus according to claim 1, wherein:
the determining unit:
performs ECG-Prep imaging multiple times to collect a plurality of images at the different cardiac phases while changing a delay time from a synchronization signal, and
determines the second period from a transition of signal values analyzed on the basis of the images collected by the ECG-Prep imaging, and the imaging unit:
performs, within the second period, imaging for multiple times at the intervals satisfying the second temporal resolution by using an FBI imaging method to depict blood pumped out of a heart.

5. The magnetic resonance imaging apparatus according to claim 1, wherein:
the determining unit:
performs BBTI-Prep imaging multiple times to collect a plurality of images at the different phases while changing a BBTI (black-blood time to inversion) time from a synchronization signal,
displays on a display the images collected by the BBTI-Prep imaging or a transition of signal values analyzed on the basis of the images, and
determines the second period by accepting an operator specification, based on the display, of a period, and
the imaging unit:
performs, in the second period, imaging for multiple times at the intervals satisfying the second temporal resolution by using a Time-SLIP (time-spatial labeling inversion pulse) imaging method in which a signal value of the fluid flowing into or flowing out of an imaging area is increased or reduced by labeling the fluid flowing into or flowing out of the imaging area in a position independent of the imaging area.

6. The magnetic resonance imaging apparatus according to claim 1, wherein:
the determining unit:
performs BBTI-Prep imaging multiple times to collect a plurality of images at the different phases while changing a BBTI time from a synchronization signal, and
determines the second period from a transition of a signal value analyzed on the basis of the images collected by the BBTI-Prep imaging, and
the imaging unit:
performs, in the second period, imaging for multiple times at the intervals satisfying the second temporal resolution by using a Time-SLIP imaging method in which a signal value of the fluid flowing into or flowing out of an imaging area is increased or reduced by labeling the fluid flowing into or flowing out of the imaging area in a position independent of the imaging area.

7. The magnetic resonance imaging apparatus according to claim 1, wherein the determining unit:
calculates a flow velocity of the fluid on the basis of the collected images, and
determines the second period from the calculated flow velocity.

8. The magnetic resonance imaging apparatus according to claim 7, wherein:
the determining unit specifies a distance traveled by the fluid by using the collected images as well as acquiring an elapsed time corresponding to the specified traveled distance from pulse sequence information used for the imaging at the first temporal resolution,
calculates a flow velocity of the fluid by dividing the traveled distance by the elapsed time, and
determines the second period on the basis of the calculated flow velocity.

9. A magnetic resonance imaging apparatus comprising:
a determining unit configured to determine, when a fluid traveling through a subject has been imaged multiple times within a first period at different phases of a subject's cardiac cycle, a second period of the cardiac cycle on a time axis within which further imaging of the fluid is to be performed; and an imaging unit configured to perform imaging of the fluid multiple times within the determined second period, wherein:

the determining unit determines the second period on the time axis within which further imaging of the fluid is to be performed, on the basis of cardiac information collected from the subject, so that the second period is included in a part of the first period in which signal values determined based upon images obtained for the different phases of the cardiac cycle within the first period rapidly change from systole to diastole.

10. A magnetic resonance imaging method to be executed by a magnetic resonance imaging apparatus, the method comprising:

imaging a fluid traveling through a subject for multiple times at different phases of the subject's cardiac cycle at a first temporal resolution covering a first period of the cardiac cycle;

determining, when the fluid has been imaged for multiple times at the different phases at the first temporal resolution, on the basis of a plurality of images collected at the first temporal resolution, a second period of the cardiac cycle on a time axis within which imaging is performed at an interval satisfying a second temporal resolution above the first temporal resolution, the second period being included in the first period on the time axis; and imaging the fluid for multiple times at the second temporal resolution at the second period.

* * * * *